(12) United States Patent
Oh et al.

(10) Patent No.: US 9,759,608 B2
(45) Date of Patent: Sep. 12, 2017

(54) COLOR DIFFERENCE METER MODULE CAPABLE OF PERFORMING REAL-TIME ZERO POINT ADJUSTMENT AND COLOR MEASURING DEVICE USING SAME

(71) Applicant: ANI. Co. Ltd., Hwaseong-si, Gyeonggi-do (KR)

(72) Inventors: Byung Jun Oh, Suwon-si (KR); Kyu Ho Lee, Yongin-si (KR); Kyu Seok Kim, Suwon-si (KR); Sun Ho Cho, Suwon-si (KR)

(73) Assignee: ANI. Co. Ltd., Hwaseong-si, Gyeonggi-do (KR)

( * ) Notice: Subject to any disclaimer, the term of this patent is extended or adjusted under 35 U.S.C. 154(b) by 0 days.

(21) Appl. No.: 14/760,256

(22) PCT Filed: Oct. 13, 2014

(86) PCT No.: PCT/KR2014/009566
§ 371 (c)(1),
(2) Date: Jul. 10, 2015

(87) PCT Pub. No.: WO2015/141918
PCT Pub. Date: Sep. 24, 2015

(65) Prior Publication Data
US 2016/0377483 A1    Dec. 29, 2016

(30) Foreign Application Priority Data
Mar. 17, 2014 (KR) .......... 10-2014-0030874

(51) Int. Cl.
*G01N 21/25* (2006.01)
*G01J 3/51* (2006.01)
(Continued)

(52) U.S. Cl.
CPC ............ *G01J 3/51* (2013.01); *G01J 1/1626* (2013.01); *G01J 3/50* (2013.01); *G01J 3/506* (2013.01);
(Continued)

(58) Field of Classification Search
CPC ........ G01J 3/51; G01J 3/524; G01J 2001/444; G01N 21/274
See application file for complete search history.

(56) References Cited

U.S. PATENT DOCUMENTS 4,131,367 A    12/1978 French et al.
6,803,555 B1 * 10/2004 Parrish ...................... G01J 1/46
250/214 AG (Continued)

FOREIGN PATENT DOCUMENTS

JP        2844692 B2    1/1999
JP    2005-265846 A    9/2005

OTHER PUBLICATIONS

International Search Report issued Dec. 30, 2014 in International Application No. PCT/KR2014/009566.

*Primary Examiner* — Michael A Lyons
*Assistant Examiner* — Maurice Smith
(74) *Attorney, Agent, or Firm* — Panitch Schwarze Belisario & Nadel LLP (57) ABSTRACT

A color measuring device includes a color difference meter module. The color difference meter module includes: a main detecting unit having an optical detecting unit configured to receive light introduced from an incident lens to generate a first current depending on a color, a first measuring unit configured to measure the first current, a sub-detecting unit having a dark detecting unit disposed adjacent to the main detecting unit and blocking the light to generate a second current in a dark state, a second measuring unit configured to measure the second current, a leakage measuring unit (Continued)

including a charging unit provided in the second measuring unit and charged with a predetermined set current, and measures a third current leaking from the charging unit, and a control unit that corrects the first current by reflecting the second current and the third current.

19 Claims, 7 Drawing Sheets

(51) Int. Cl.
*G01J 3/52* (2006.01)
*G01N 21/27* (2006.01)
*G01J 1/16* (2006.01)
*G01J 3/50* (2006.01)
*G01J 1/44* (2006.01)

(52) U.S. Cl.
CPC ............ *G01J 3/524* (2013.01); *G01N 21/274* (2013.01); *G01J 2001/444* (2013.01)

(56) References Cited

U.S. PATENT DOCUMENTS

| | | | | |
|---|---|---|---|---|
| 7,098,443 B2* | 8/2006 | Tan | ................. | G01J 3/524 |
| | | | | 250/226 |
| 7,435,943 B1* | 10/2008 | Chen | ................. | G01J 3/51 |
| | | | | 250/214.1 |
| 2005/0200732 A1* | 9/2005 | Tan | ................. | G01J 1/0252 |
| | | | | 348/243 |
| 2010/0060562 A1* | 3/2010 | Hadwen | ............ | H01L 31/02164 |
| | | | | 345/102 |
| 2014/0353471 A1* | 12/2014 | Raynor | ................ | G01J 1/1626 |
| | | | | 250/214 C |

* cited by examiner

Fig. 1

Prior Art

COLOR DIFFERENCE METER MODULE CAPABLE OF PERFORMING REAL-TIME ZERO POINT ADJUSTMENT AND COLOR MEASURING DEVICE USING SAME

CROSS-REFERENCE TO RELATED APPLICATION

This application is Section 371 of International Application No. PCT/KR2014/009566, filed Oct. 13, 2014, which claims the benefit of Korean Patent Application No. 10-2014-0030874, filed Mar. 17, 2014, the disclosures of which are incorporated herein by reference.

BACKGROUND OF THE INVENTION

Technical Field

The present invention relates to a color measuring device. More particularly, it relates to a color difference meter module capable of reducing an error caused by changes in environmental factors during an exposure time so as to accurately measure the characteristics of color of a color display panel, and a color measuring device using the same.

Background Art

Currently, a world monitor market has rapidly changed from CRT to LCD monitor, and from LCD to LED monitor. Especially, as the demand for a large-scale LED monitor has increased, an amount of production has rapidly increased.

As the amount of production of the displays has increased, the production quality has also acted as important factors, and devices for determining whether there is a failure of the device have been developed. In particular, color difference meters for measuring whether the color represented by a display such as LCD or LED fully represents color to be actually output were developed.

Although a general color difference meter is configured to measure the color of light that is incident through a detection sensor constituted by an optical detecting unit, numerical values detected depending on changes in the external environment factors will change, in view of the characteristics of the optical detecting unit.

To solve such a problem, conventionally, the zero point has been frequently adjusted and used immediately before the use of the color difference meter.

In particular, conventionally, there has been a need to adjust the zero point after necessarily completely blocking the light to be incident at the measurement environment for accurate measurement values.

Figure 1:
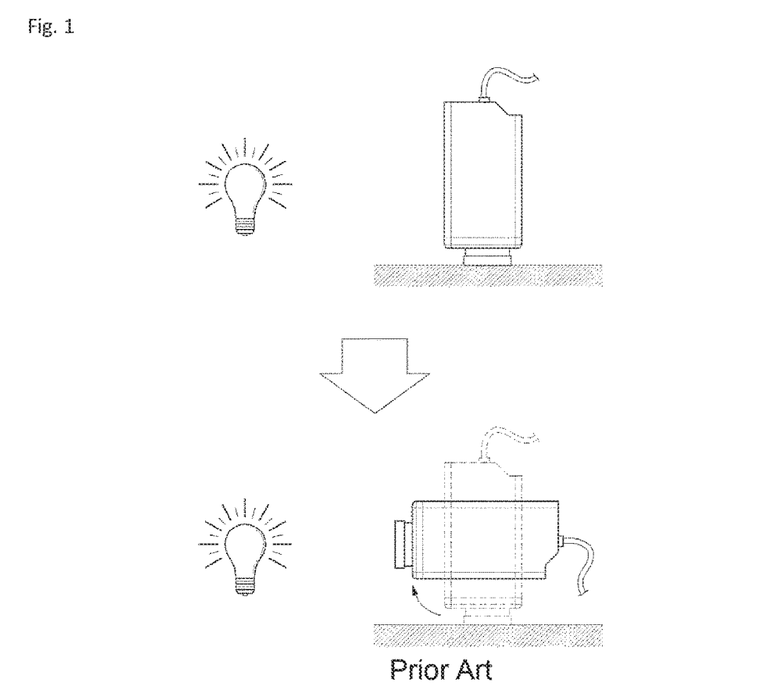
FIG. 1 is a drawing schematically illustrating a configuration of a conventionally used color measuring device.

Specifically, as illustrated in FIG. 1, a conventional color measuring device has been brought into contact with a dark cover or a floor to prevent the light from being incident on the interior, and has adjusted the zero point in such a state. Moreover, after adjusting the zero point in this way, the color of the light emitted from a measurement target is measured.

However, when adjusting the zero point using such a method, there has been an inconvenience such as a need to always adjust the zero point during the color measurement.

Furthermore, there has been a problem such as changes in the values measured by the changes in temperature and humidity during measurement of the color after the zero point adjustment, resulting in a decrease in accuracy. In particular, since the leakage current from a circuit basically applied to the color measuring device greatly changes due to changes in the external environmental factors, the color measurement has not been accurately performed.

Also, since it is necessary to frequently adjust the zero point in production sites when performing the zero point adjustment in the conventional manner, there has been a problem of a decrease in productivity.

DISCLOSURE

Technical Problem

The present invention has been made to solve the problems of the conventional color measuring device, and an aspect of the present invention provides a color difference meter module that is capable of accurately measuring the color of light to be measured by including therein a separate sub-detecting unit for measuring a signal detected in a dark state apart from a main detecting unit, and a color measuring device using the same.

Technical Solution

In order to solve the above-mentioned problems, according to an aspect of the present invention, there is provided a color measuring device that includes a case having a light sensing space formed therein; an incident lens module that is configured by continuous arrangement of a plurality of lenses in an inward direction on one side of the case and is disposed in a region in which light is emitted from a measuring target to transmit the emitted light into the interior; and a color difference meter module that includes a main detecting unit having an optical detecting unit configured to receive the light introduced from the incident lens to generate current depending on the color and a first measuring unit configured to measure a first current generated by the optical detecting unit, a sub-detecting unit having a dark detecting unit disposed adjacent to the main detecting unit and blocking light to generate a current in the dark state and a second measuring unit configured to measure a second current generated by the dark detecting unit, a leakage measuring unit that has a charging unit provided in the second measuring unit and charged with a predetermined set current and measures a third current leaking from the charging unit, and a control unit that corrects the first current by reflecting the second current measured by the sub-detecting unit and the third current measured by the leakage measuring unit, wherein the charged current in the charging unit decreases during the time at which the main detecting unit receives light to generate the first current, and the third current leaks.

Further, in the leakage measuring unit, while receiving the light from the incident lens to measure the color, the third current leaks from the set current charged in the charging unit and, after the completion of the color measurement, all the residual current remaining in the charging unit is removed, and the set current is charged to the charging unit again.

Here, the leakage measuring unit may measure a difference between the set current and the residual current to detect the amount of the leaked third current.

The first measuring unit may include a leakage measuring unit having the same shape as the second measuring unit.

The sub-detecting unit may be affected by the same conditions as the main detecting unit affected by external factors.

The main detecting unit may include at least three or more optical detecting units, and each of them may be configured to detect light of wavelengths different from each other.

The color difference meter module may further include a connector that is disposed in front of the main detecting unit and includes a communication port that is in communication with the main detecting unit to transmit the incident light to the main detecting unit; a color filter that is provided inside the communication port to transmit only light of a specific wavelength from the incident light; and a filtering unit that causes the light incident on each of the optical detecting units to have wavelengths different from each other.

The color measuring device may further include an optical distribution module provided between the incident lens module and the color difference meter module to distribute and transmit the light incident from the incident lens module to the color difference meter module.

According to another aspect of the present invention, there is provided a color difference meter module that includes a main detecting unit which includes an optical detecting unit configured to receive the light introduced from an incident lens to generate current depending on the color, and a first measuring unit configured to measure a first current generated by the optical detecting unit; a sub-detecting unit that is disposed adjacent to the main detecting unit and includes a dark detecting unit configure to block light to generate a current in a dark state, and a second measuring unit configured to measure a second current generated by the dark detecting unit; a leakage measuring unit that includes a charging unit provided in the second measuring unit and charged with a predetermined set current, and measures a third current leaking from the charging unit; and a control unit that corrects the first current by reflecting the second current measured by the sub-detecting unit and the third current measured by the leakage measuring unit, wherein the charged current of the charging unit decreases depending on a change in time at which the main detecting unit and the sub-detecting unit receive light to generate current, and the third current leaks.

The leakage measuring unit may measure the leaked third current by passing through a first measurement process in which the third current leaks from the set current charged in the charging unit while receiving the light from the incident lens to measure the first current by the first measuring unit, and a second measurement process in which all the residual current remaining in the charging unit is removed after completion of the first measurement process.

The leakage measuring unit may measure the difference between the set current and the residual current to measure the leaked third current.

Furthermore, the third current may be derived by following Formula 1.

$$D_\Delta = D_c - D_d \qquad \text{Formula 1}$$

($D_\Delta$=third current, $D_c$=set current, and $D_d$=residual current)

Also, the control unit may correct the first current using the second current and the third current and may measure the color of the light incident on the main detecting unit from the incident lens through the corrected first current.

The control unit may measure the color of the light incident on the main detecting unit by correcting the first current by formula 2 below.

$$A' = A - A_d - D_\Delta \qquad \text{Formula 2}$$

(A'=corrected first current, A=first current, $A_d$=second current, and $D_\Delta$=third current)

The first measuring unit may be provided with the leakage measuring unit of the same shape as that provided in the second measuring unit.

Further, the sub-detecting unit may be affected by the same conditions as the main detecting unit affected by external factors.

The main detecting unit may include at least three or more first measuring units, and each of them may be configured to detect light of wavelengths different from each other.

The color measuring device may further include a separate filtering unit that is installed in front of the main detecting unit to cause the light incident on each of the optical detecting units to have wavelengths different from each other.

Further, the filtering unit may include a connector that is installed in front of the main detecting unit, and includes a communication port that is in communication with the main detecting unit to transmit the incident light to the main detecting unit; and a color filter that is provided inside the communication port to transmit only light of a specific wavelength from the incident light.

Advantageous Effect

According to the present invention for solving the above problems, there are following effects.

First, by providing the main detecting unit for measuring the first current generated by light incident on the color measuring device, and the sub-detecting unit for measuring the second current generated in the dark state, there is an effect of being able to measure the accurate color through a relative comparison between the detected first current and the second current, without passing through another zero point adjustment process.

Second, by providing the leakage measuring unit of the same structure on each of the main detecting unit and the sub-detecting unit and by measuring the third current leaking from the sub-detecting unit using the leakage measuring unit to correct the first current, there is an effect of being able to accurately measure the color of light incident on the main detecting unit by removing the amount of current leaking from the first current.

Third, since the main detecting unit and the sub-detecting unit simultaneously measure the first current and the second current without separate zero point adjustment, the value detected by the time difference does not vary, and there is the effect of increases in accuracy and reliability of the measured color.

The effects of the present invention are not limited to the foregoing effects, and other effects that have not mentioned will be clearly understood to those skilled in the art from the scope of the claims.

BRIEF DESCRIPTION OF THE DRAWINGS

The above objects, other features and advantages of the present invention will become more apparent by describing the preferred embodiments thereof with reference to the accompanying drawings, in which.

PREFERRED EMBODIMENTS OF THE INVENTION

Preferred embodiments of a color difference meter module according to the present invention and a color measuring device using the same will be described through accompanying drawings. However, this is not intended to limit the invention to the particular form but to assist the clearer understanding throughout the embodiments.

Further, in describing the present embodiment, the same configurations are denoted by the same names and the same reference numerals, and additional description of them will not be provided.

First, a color measuring devices according to the embodiment of the present invention will be described below referring to FIGS. 2 to 6.

Figure 2:
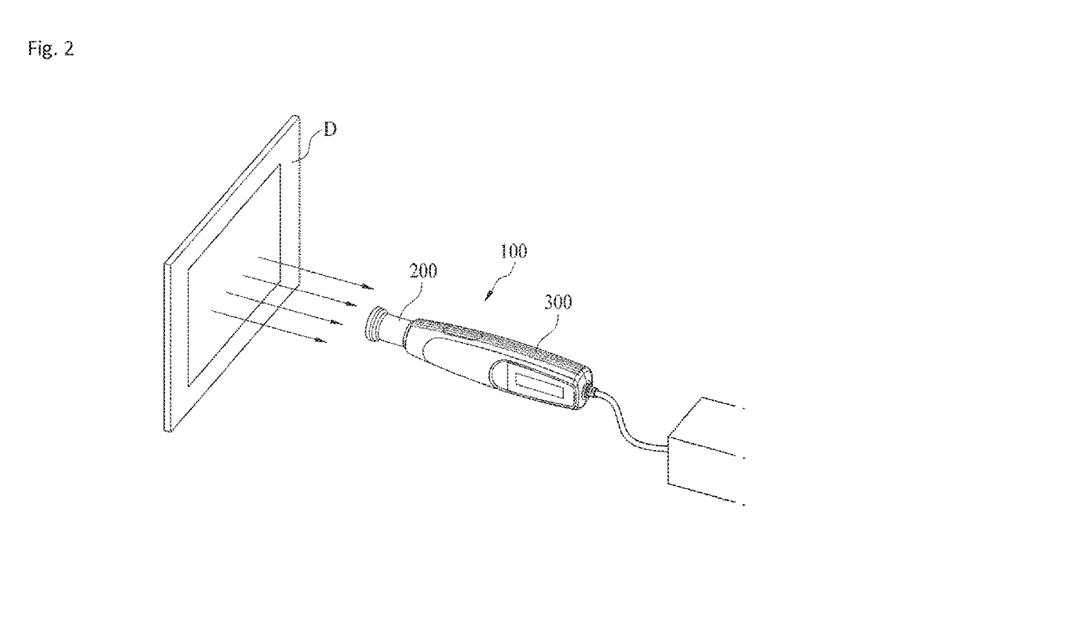
FIG. 2 is a diagram illustrating a state of using a color measuring device according to an embodiment of the present invention.
Figure 3:
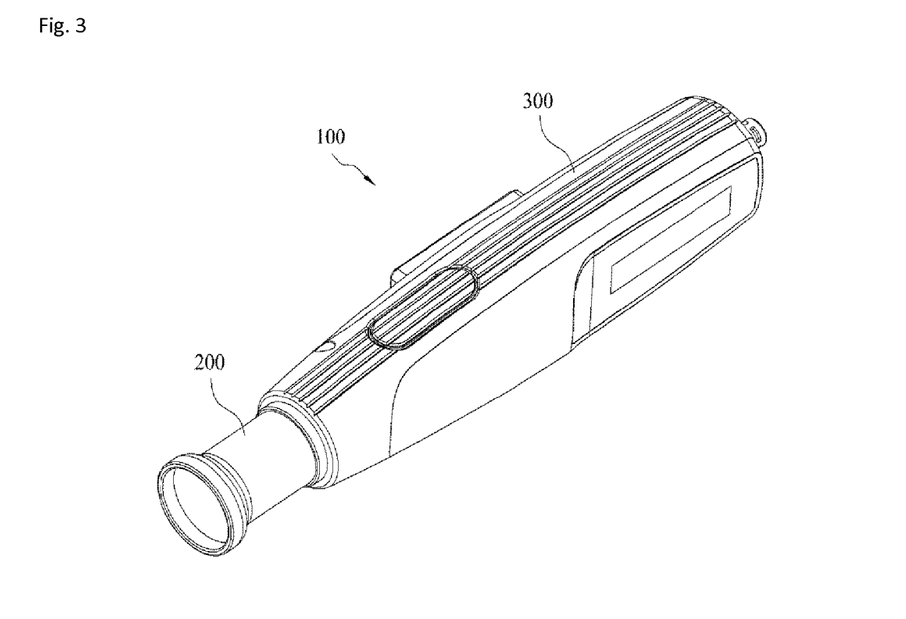
FIG. 3 is a diagram illustrating an external form of the color measuring device of FIG. 2.
Figure 4:
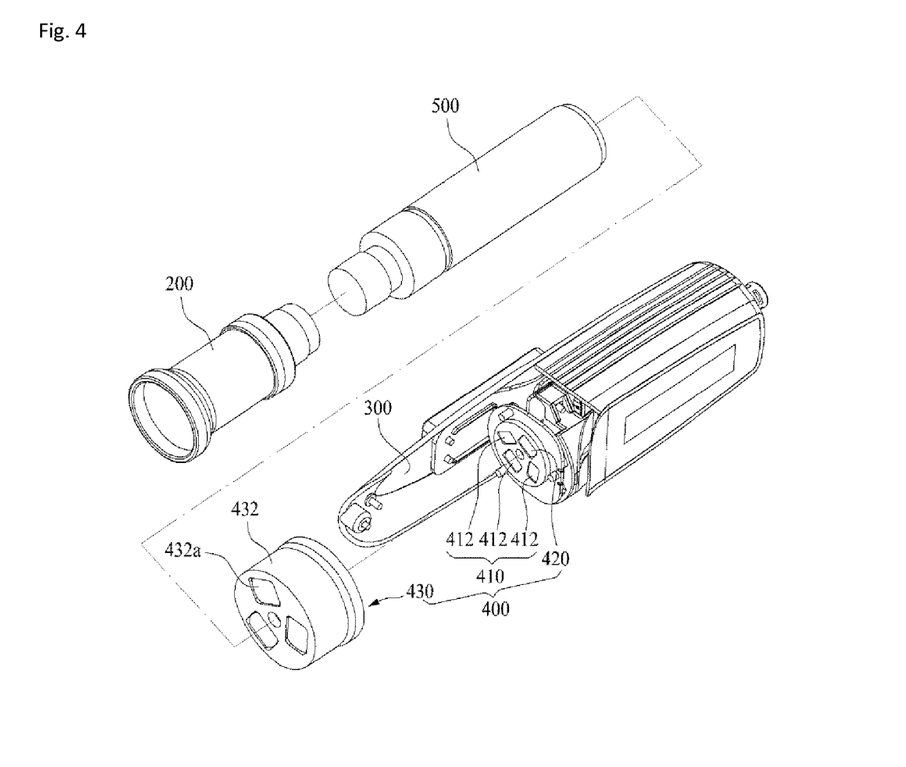
FIG. 4 is a diagram illustrating an internal configuration of the color measurement device of FIG. 2.

FIG. 2 is a diagram illustrating a state of using the color measuring device according to an embodiment of the present invention, FIG. 3 is a diagram illustrating an external form of the color measuring device of FIG. 2, and FIG. 4 is a diagram illustrating an internal configuration of the color measuring device of FIG. 2.

Figure 5:
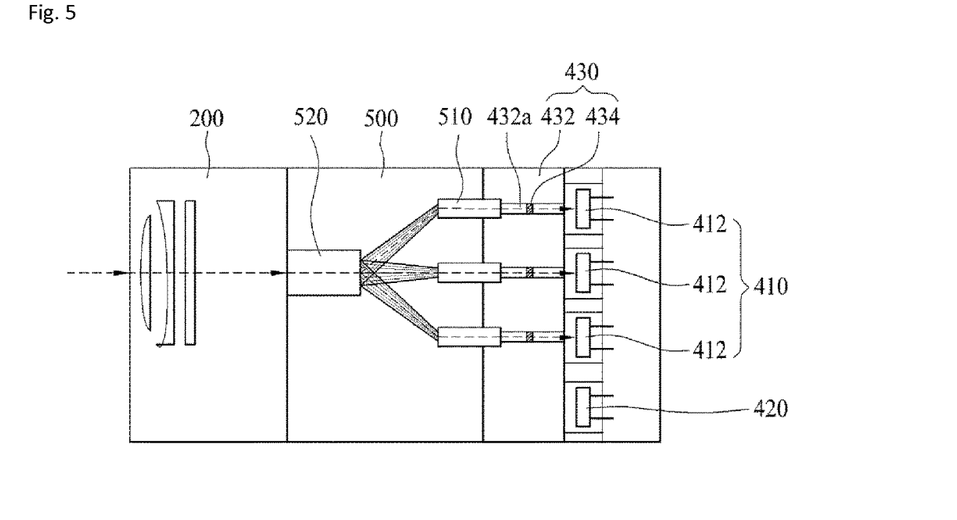
FIG. 5 is a diagram of a state in which the color difference meter module detects the light in the color measuring device of FIG. 2.
Figure 6:
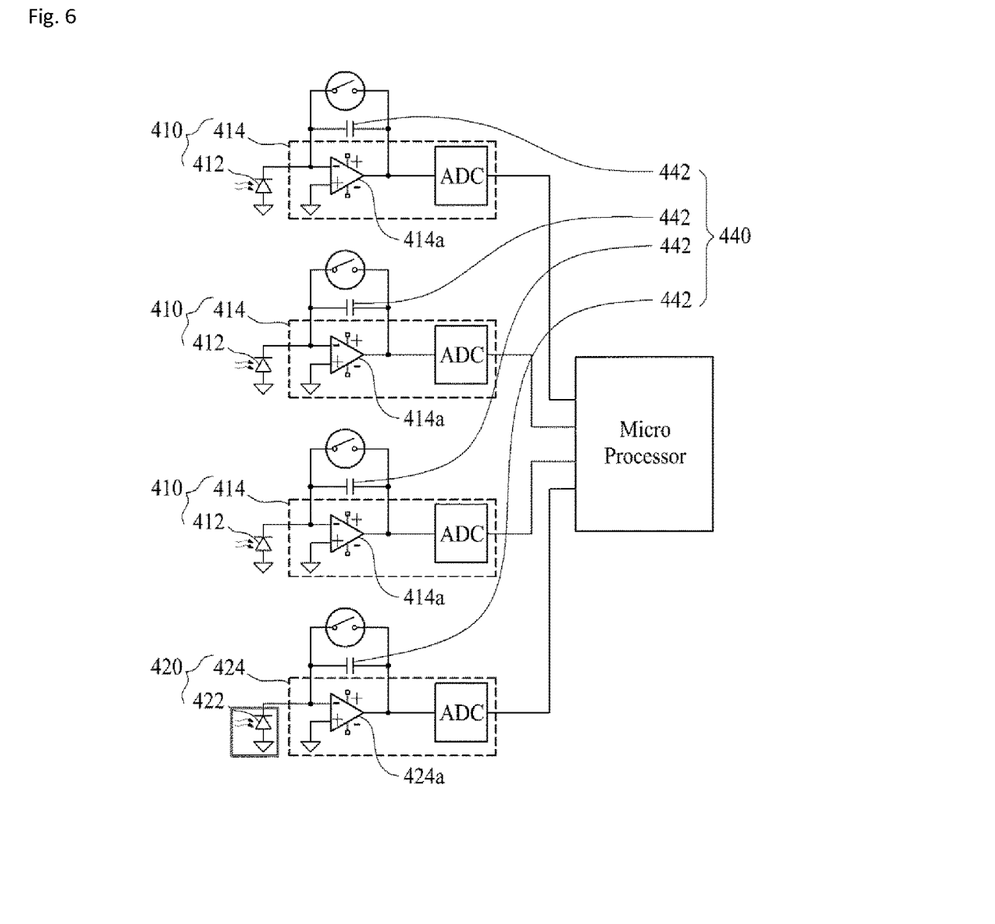
FIG. 6 is a diagram illustrating a configuration of leakage measuring units that are installed in each of the main detecting unit and the sub-detecting unit in the color measurement device of FIG. 2.

FIG. 5 is a diagram illustrating a state in which the color difference meter module detects the light in the color measuring device of FIG. 2, and FIG. 6 is a diagram illustrating the configuration of leakage measuring units installed in each of the main detecting unit and the sub-detecting unit in the color measuring device of FIG. 2.

As illustrated, a color measuring device 100 according to an embodiment of the present invention is configured to generally include a case 300, an incident lens module 200, a color difference meter module 400, and an optical distribution module 500.

The case 300 surrounds the whole, a light sensing space is formed inside, and the incident lens module 200 is located on one side. Moreover, the optical distribution module 500 and the color difference meter module 400 are disposed on the inner side, and each of them is provided by being separately isolated.

In this embodiment, the cylindrical light distribution module 500 and the color difference meter module 400 provided so as to be adjacent to the incident lens module 200 are provided inside the case 300.

The incident lens module 200 is located in a region in which light is emitted from the measurement target D on one side of the case 300 to transmit the emitted light into the interior.

Here, the incident lens module 200 is formed in a shape in which multiple different lenses are successively disposed, thereby condensing and transmitting the light emitted from the measurement target D to the interior of the case 300.

The light distribution module 500 is provided between the incident lens module 200 and the color difference meter module 400, distributes and transmits the light incident from the incident lens module 200 to the color difference meter module 400.

At this time, in this embodiment, as illustrated, when measuring the color, the color is measured using three stimulus values, and may be configured in various ways without being limited thereto.

Thus, the light distribution module 500 splits and transmits the light having the same wavelength and intensity as the incident light to the color difference meter module 400, and the transmitted light is configured so that the light transmitted to each of three optical detecting units 412 by a separate color filter (434, see FIG. 5) is transmitted while having different wavelengths.

In this embodiment, the light distribution module 500 is provided inside the cylindrical cover as described above, and the cylindrical cover is disposed inside the case 300. Its one side is disposed adjacent to the incident lens module 200, and the other side is disposed adjacent to the color difference meter module 400.

Specifically, as illustrated in FIG. 5, the light distribution module 500 is constructed to include a plurality of optical fibers (510, see FIG. 5), and the optical fiber 510 is provided with an optical transmission unit (520, see FIG. 5) for transmitting the light, which is incident through the incident lens module 200, to the optical fiber 510.

The optical transmission unit 520 receives and transmits the light incident through the incident lens module 200 to the plurality of optical fibers 510. Here, since the optical transmission unit 520 is generally formed to be smaller than the incident lens module 200, in order to receive all the light transmitted from the incident lens module 200, the incident lens module 200 refracts and transmits the incident light to the optical transmission unit 520.

The optical fiber 510 is composed of a plurality and is disposed in the same direction, one sides are disposed densely to each other and are connected to the optical transmission unit 520, and is transmitted to the optical fiber 510 incident through the optical transmission unit 520. Moreover, the other sides of the plurality of optical fibers 510 are divided into three major groups, and each group consists of optical fiber 510 having the same size and number and is transmitted to the color difference meter module 400 to be described below.

In this embodiment, the plurality of optical fibers 510 has the same size, the other sides are divided into three groups, and each group has all the same number.

Since all the optical fibers 510 have the same size, even if the other side is divided into three groups, when maintaining the same number, the light transmitted to each of the color difference meter modules 400 can have the same wavelength and intensity. However, it is not particularly limited to this form. Even if each of the optical fibers 510 has different sizes, as long as they are configured to be able to transmit light of the same wavelength and intensity to each of the color difference meter modules 400, any form can be applied.

In this way, the light distribution module 500 evenly transmits light, which is incident between the incident lens module 200 and the color difference meter module 400, to each of the color difference meter modules 400.

Meanwhile, when the light distribution module 500 uses the optical fiber 510, the loss of light can be reduced, and it has a feature that can be flexibly bent. Thus, even if the color difference meter module 400 and the light distribution module 500 are not disposed on a straight line, it is possible to increase the utilization of space.

The color difference meter module 400 measures the color of light of the relevant wavelength by detecting the light incident from the incident lens module 200, and largely has a main detecting unit 410, a sub-detecting unit 420, a leakage measuring unit 440, and the control unit (not illustrated).

Specifically, the main detecting unit 410 has a configuration that receives the light that is incident through the incident lens module 200 to detect the color, and includes a first detecting unit 414 that measures a first current A generated by the optical detecting unit 412 and detection of light in the optical detecting unit 412, by providing at least one or more optical detecting units 412.

Specifically, the optical detecting unit 412 receives the light incident from the light incident lens module 200 within the case 300 to generate a current depending on the color.

In this embodiment, the optical detecting unit 412 uses a photo diode as a kind of sensor that converts the light into an electric signal by receiving the light, and receives the light, which is incident through the incident lens module 200, and converts the received light into the electrical signal. Thus, the received electrical signals are used to measure the color of the received light by a separate external device.

The first measuring unit 414 has a configuration that measures a first current A generated by detecting the light in the light detecting unit 412 and thus, may measure the wavelength of the light incident on the optical detecting unit 412.

In this embodiment, this has a configuration that detects and measures the first current A generated by light incident on the light detecting unit 412. Further, additionally, as illustrated in FIG. 6, the first measuring unit 414 can further include an amplifier circuit 414a for amplifying the first current A and an ADC.

Thus, the main detecting unit 410 according to the present invention includes the light detecting unit 412 and the first measuring unit 414 to measure the first current A, depending on the light incident from the incident lens module 200.

In this embodiment, as illustrated, the main detecting unit 410 includes three optical detecting units 412, and each of them is configured to detect light of the different wavelengths.

The three first measuring units 414 are also independently configured together with the optical detecting unit 412. Thus, the light split by the optical distribution module 500 described above is transmitted to each of the optical detecting units 412, and each of the generated first currents A is measured by the first measuring unit 414.

Meanwhile, the sub-detecting unit 420 is disposed adjacent to the main detecting unit 410, and measures a second current Ad generated by the signal detected in a dark state by blocking the light. Here, the sub-detecting unit 420 includes a dark detecting unit 422 of the same shape as the main detecting unit 410 described above, and measures the second current Ad generated by the dark detecting unit 422 in the dark state of completely blocking the light that is incident from the incident lens module 200.

Specifically, the sub-detecting unit 420 includes a dark detecting unit 422 that generates the current in a dark state, and a second measuring unit 424 that measures the second current Ad generated in the dark detecting unit 422.

As described above, the dark detecting unit 422 can be configured in the same form as the optical detecting unit 412, and is configured so that the same external conditions can be applied by being disposed adjacent to the optical detecting unit 412. The dark detecting unit 422 generates the second current Ad due to changes in external conditions.

The second measuring unit 424 is configured identically to the first measuring unit 414 described above, and is configured to measure the current generated in the dark detecting unit 422.

Here, similarly to the first measuring unit 414 described above 414, the second measuring unit 424 can further include an additional amplifier circuit 424a and an ADC.

Thus, the sub-detecting unit 420 includes the dark detecting unit 422 and the second measuring unit 424, and measures the second current Ad generated in the same conditions as the main detecting unit 410.

In this embodiment, the sub-detecting unit 420 is configured to have substantially the same structure as the main detecting unit 410, and is configured so that the light is not incident on the dark detecting unit 422, and second current Ad is generated in a dark state.

Meanwhile, the leakage measuring unit 440 has a configuration that is provided in the second measuring unit 424 to measure the leakage current leaking from the second measuring unit 424.

Specifically, the leakage measuring unit 440 includes a charging unit 442 that is provided in the second measuring unit 424 and is charged with a predetermined set current Dc, and measures a third current $D_A$ leaking from the charging unit 442.

At this time, in the charging unit 442, the charged current decreases in accordance with a change in time at which the main detecting unit 410 receives light to generate the current, and the third current $D_A$ leaks.

That is, the charging unit 442 is configured so that the set current Dc charged during generation of the first current A from the main detecting unit 410 decreases, and the reduced current measures the third current $D_A$.

Here, the third current $D_A$ can be measured by measuring the difference between a set current Dc initially charged to the charging unit 442 and a residual current Dd remaining in the charging unit 442 later, and a specific process of measuring a third current $D_A$ will be described later with reference to FIG. 9.

In this embodiment, the leakage measuring unit 440 is installed independently in the first measuring unit 414 as well as in the second measuring unit 424, thereby ensuring that the main detecting unit 410 and the sub-detecting unit 420 are configured with the same conditions.

Meanwhile, although not illustrated in the drawings, the control unit corrects the first current A measured in the main detecting unit 410, by reflecting the second current Ad measured by the sub-detecting unit 420 and the third current $D_A$ measured by the leakage measuring unit 440.

Specifically, the control unit can measure the numerical value of the first current exact A, by correcting using the second current Ad measured in a state that does not detect light for improving the accuracy of the first current A measured for the exposure time in the main detecting unit 410, and the third current $D_A$ measured by the leakage measuring unit 440 during the exposure time. Specific functions of the control unit will be described below referring to FIG. 10.

In this way, the color difference meter module 400 according to the present invention includes the main detecting unit 410, the sub-detecting unit 420, the leakage measuring unit 440, and the control unit. The color difference meter module 400 can accurately measure the color of the light measured by the main detecting unit 410, by measuring each of the first current A measured by the main detecting unit 410, the second current Ad measured by the sub-detecting unit 420, and the third current $D_A$ measured by the leakage measuring unit 440, and by correcting the first current A by utilizing this in the control unit.

Meanwhile, the color difference meter module 400 according to the present invention further includes a separate filtering unit 430 that is installed in front of the main detecting unit 410 to cause the light incident on each of the optical detecting units 412 to have wavelengths different from each other.

The filtering unit 430 is disposed in front of the main detecting unit 410, and includes a connector including a communication port 432a that communicates with the main detecting unit 410 and transmits the incident light to the main detecting unit 410, and a color filter 434 that is provided inside the communication port 432a and transmits only light of a specific wavelength from the incident light.

Specifically, the filtering unit 430 has separate color filters 434 that cause the light incident on the optical detecting unit 412 provided in each of the main detecting units 410 to have wavelengths different from each other, and in the present invention, the filtering unit 430 is disposed in front of the main detecting unit 410 to transmit the light, which is divided and transmitted from the optical transmission unit 520, to the main detecting unit 410.

In this embodiment, the filtering unit 430 is disposed between the optical distribution module 500 and the main detecting unit 410 inside the case 300, and largely includes the connector 432 and the color filter 434.

The connector 432 has the shape of a cover, and is provided with a communication port 432a that communicates forward and backward, and the color filter 434 is provided inside the communication port 432a.

Specifically, the connector 432 is formed in a circular cover shape, has the number corresponding to the number of the light detecting unit 412, and is formed with a communication port 432a which communicates with the main detecting unit 410. In this embodiment, three communication ports 432a are formed, color filters 434 are provided in each of the three communication ports 432a, and are configured to transmit light of wavelengths different from each other.

Here, the communication port 432a is configured so as to communicate with each other forward and backward, one side of which is disposed so as to face the point where three optical detecting units 412 are located so as to correspond to each of the positions, and the other side is configured such that each of the optical fiber 510 divided into three groups is coupled to each other.

Thus, the light divided by the optical distribution module 500 passes through the connector 432, only light of a specific wavelength is transmitted by the color filter 434 provided therein, and the transmitted light is transmitted to the optical detecting unit 412 to generate the first current A.

Here, the connector 432 is configured such that the communication port 432a is disposed so as not to communicate with the position of the sub-detecting unit 420 described later, and the connector 432 itself serves as a blocking wall that blocks the light.

That is, each of the light distributed from the light distribution module 500 by the connector 432 is configured so as to be transferred to the three optical detecting units 412 rather than the sub-detecting unit 420.

However, unlike this, the color filter 434 may be directly disposed in front of the light detecting unit 412, without being equipped inside the connector 432.

Meanwhile, the color filter 434 according to the present invention receives light transmitted from the incident lens module 200 and transmits only light of a specific wavelength. At this time, as the color filter 434, filters of various types and structures can be used, and in the present embodiment, an interference filter is used.

The interference filter refers to a filter that filters the wave of a specific wavelength by utilizing the interference phenomena that occurs on a thin film. It is divided into several types depending on the methods and types of the filter materials to obtain the desired wave.

In general, the color difference meter module 400 measures the color by utilizing a tristimulus value through a standard observer as defined in Commission International de l'Eclairage (CIE).

The tristimulus value is a value serving as a reference value that represents light indicated on the color of light recognized through the three cone cells that detect light of wavelengths different from each other in the human's eye.

Thus, so as to accurately measure each of the tristimulus values, lights of three regions of X, Y, and Z as tristimulus values are separated, separately to measure the color through the first current A generated by the light detecting unit 412.

To measure the color of light of respective tristimulus values in this way, each of the color filters 434 is configured so as to transmit only light of respective wavelengths different from each other of the tristimulus values.

Thus, the color difference meter module 400 is provided inside of the case 300 to detect an electrical signal of the light of a particular wavelength among the light incident through the incident lens module 200, thereby allowing the external device to detect the color therethrough.

The color measuring device 100 as configured above is configured so that the light distribution module 500 and the color difference meter module 400 are continuously disposed inside the case 300.

Meanwhile, as illustrated in FIG. 2, the color measuring device 100 having the above configuration is disposed so that the incident lens module 200 is located in a region where the light is emitted from the one side of the measurement target D and light is incident on the inside of the color measuring device 100. Here, as illustrated, although the color measuring device 100 can be used by being mounted to a particular location, it can be configured so as to be useable at a desired location by being separately carried without being particularly mounted.

Thus, the color measuring device 100 according to the present invention can measure the color of the incident light, by utilizing the first current A to the third current $D_A$ measured by each of the main detecting unit 410, the sub-detecting unit 420, and the leakage measuring unit 440.

Meanwhile, more specifically, specifically considering a state of detecting the color of light from the color measuring device 100 according to the present embodiment, as illustrated in FIG. 5, light is incident through the incident lens module 200. The incident light is distributed through the optical transmission unit 520 and is transmitted to each of the optical fibers 510 divided into three pieces.

Each light distributed by the optical distribution module 500 moves through the communication port 432a formed in the connector 432, and transmits light of wavelengths different from each other by the color filter 434.

Thus, the light filtered while passing through each communication port 432a is incident on the optical detecting unit 412 connected to each of the communication ports 432a, each of the optical detecting units 412 generates the first current A corresponding to the incident light, and measures the first current A by the first measuring unit 414 and transmits it to the control unit.

Meanwhile, the sub-detecting unit 420 measures the second current Ad generated by the dark detecting unit 422 in the dark state when detecting light in the light detecting unit 412 during the light exposure time although there is no incident light by the second measuring unit 424, and transmits it to the control unit.

When the main detecting unit 410 and the sub-detecting unit 420 measure the first current A and the second current Ad, the leakage measuring unit 440 measures the third current $D_A$ leaking from the second measuring unit 424 during the exposure time and transmits it to the control unit.

The control unit which receives the measured first current A though the third current $D_A$ corrects the first current A, by utilizing the second current Ad and the third current $D_A$.

Specifically, the first current A is a value obtained by measuring the current generated depending on the color of light that is incident and detected from the main detecting unit 410, and includes values changed by external environmental factors such as temperature and humidity as well as the simply incident light.

Moreover, the second current Ad is a value obtained by measuring the current generated in the dark detecting unit 422 by changes in the external environmental factors such as temperature and humidity in the sub-detecting unit 420 in the dark state.

Thus, the first current A is corrected in the control unit using the respectively measured first current A and the second current Ad and is transmitted to the external device, thereby measuring the accurate color.

In particular, since the error of the value detected by a change in temperature or humidity is high in the optical detecting unit 412, the first current A measured by the main detecting unit 410 is in the state of weak reliability. Thus, the control unit ensures the reliability of the measurement value of the first current A, by correcting the first current A as much as the second current Ad.

Furthermore, in the present invention, the color difference meter module 400 includes the leakage measuring unit 440, and the sub-detecting unit 420 measures the third current $D_A$ leaking by the external environmental factors, it is transmitted to the control unit, and thus, the control unit corrects the first current A, using the third current $D_A$ as well as the second current Ad when correcting the first current A.

That is, the color measuring device 100 according to the present invention corrects the first current A generated by the light incident on the main detecting unit 410 using both the second current Ad and the third current $D_A$ in the control unit. Thus, it is possible to measure the color of the incident light, by accurately measuring the actual current value generated by light incident on the color difference meter module 400 during the exposure time.

In fact, a amount of change in the third current $D_A$ leaking during the exposure time by the configuration of the main detecting unit 410 and the sub-detecting unit 420 in response to changes in the external environmental factors caused by temperature and humidity is relatively larger than an amount of change in the first current A and the second current Ad generated by the optical detecting unit 412 and the dark detecting unit 422.

Thus, the first current A is corrected using the third current $D_A$ detected by leakage measuring unit 440 as well as the second current Ad detected by the sub-detecting unit 420 through the control unit. Thus, it is possible to measure more accurate the first current A, and thus, it is possible to more accurately measure the color incident on the main detecting unit 410.

Subsequently, referring to FIGS. 7 and 8, as described above, the state in which the leakage current leaking from main detecting unit 410 and the sub detecting unit 420 varies by the external environmental factors will be described as follows.

Figure 7:
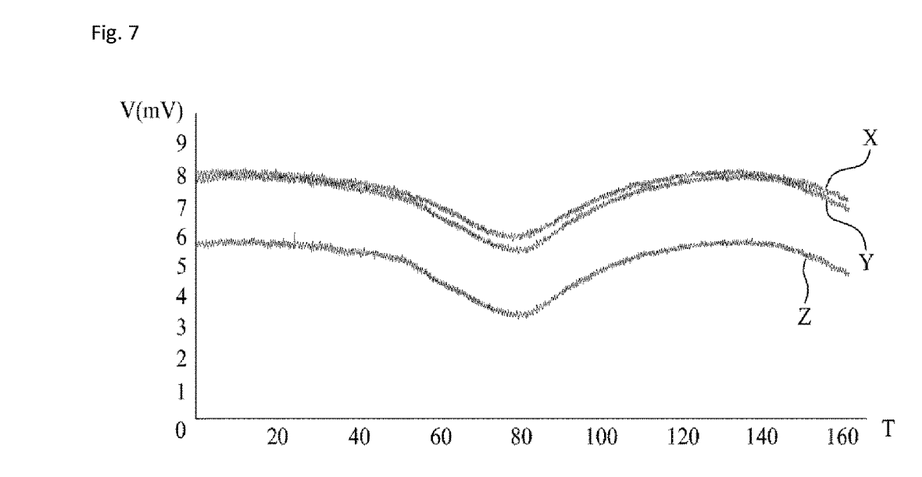
FIG. 7 is a graph illustrating a state in which a stimulus value detected by the main detecting unit of FIG. 6 varies by the leakage current generated depending on the changes in external factors.
Figure 8:
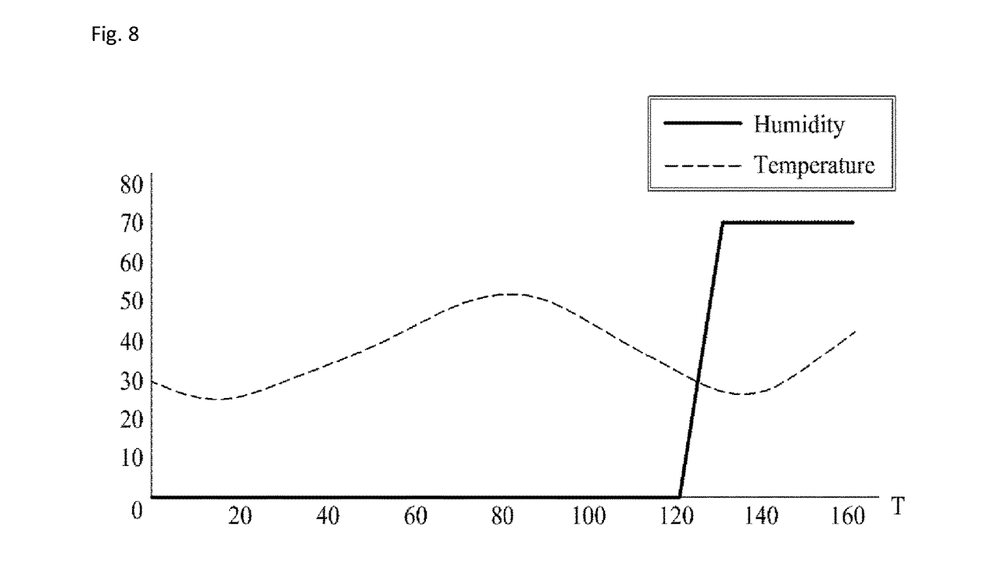
FIG. 8 is a graph illustrating changes in external conditions over time for the experiment of FIG. 7.

FIG. 7 is a graph illustrating a state in which a stimulus value detected by the main detecting unit 410 of FIG. 6 varies with the leakage current generated depending on changes in external factors, and FIG. 8 is a graph illustrating changes in external conditions over time for the experiment of FIG. 7.

Looking at the illustrated drawings, these are graphs indicated by testing the amount of change in the first current A which is measured depending on changes in temperature and humidity, and X, Y and Z as the tristimulus values are derived through the first current A measured by measuring the light of the same color using the color measuring device 100.

At this time, as described above in this embodiment, the first current A is a current generated by causing the light of wavelengths different from each other to be incident on the three main detecting units 410 by the filtering unit 430.

Test conditions are as follows, and it is possible to know that the tristimulus values of X, Y, and Z derived depending on the changes in humidity and temperature. Here, the tristimulus value is a value represented using a voltage derived using the first current A measured by the main detecting unit 410.

Temperature range: 20 to 50 degrees
Humidity range: 0 to 70%
Test Duration: 160 minutes
Exposure time: 200 ms
X, Y, Z voltage units: mV More specifically, as illustrated in the graph of FIG. 7, it is possible to know that the amount of the first current A generated by the main detecting unit 410 changes according to time. As illustrated in FIG. 8, this is measured by reflecting the changes in temperature and humidity conditions of the main detecting unit 410, and it is possible to know that as the temperature and humidity of the main detecting unit 410 increase, the amount of leakage current increases, and thus, the measured first current A changes, and the voltage of the tristimulus values changes.

In particular, when comparing the tristimulus values in the case where the temperature of the main detecting unit 410 is 50 degrees and 25 degrees, it is possible to know that the voltage difference more than about 2 mV is generated in the case of 50 degrees, as compared to the case of the temperature of 25 degrees of the main detecting unit 410.

This is a difference that cannot be represented merely by the extent that the first current A measured by the optical detecting unit 412 through the change in external environmental factors, and this is a change in the first current A measured by the leakage current generated in the main detecting unit 410.

In other words, the main detecting unit 410 includes a change in the first current A measured in the first measuring unit 414 depending on the change of the leakage current, generation of the leakage current in the amplification circuit 414a or the like included therewith, as well as a change in the first current A generated in the optical detecting unit 412 in the form of typical photodiode by external environmental factors.

Further, the third current $D_A$ leaking from the charging unit 442 significantly changes depending on changes in the external environment factors, and thus, the first current A measured by the first measuring unit 414 significantly changes.

Thus, the first current A measured by the main detecting unit 410 by the light incident on the optical detecting unit 412 changes in the value of the first current A measured depending on the changes in external environmental factors, and an influence of the leakage current changes depending on the external environment on the first current A is greater than an influence of the optical detecting unit 412 itself on the first current A by the changes in the external environmental factors.

Furthermore, the third current $D_A$ itself leaking from the charging unit 442 greatly changes depending on changes in the external environment factors, and significantly effects on the measured value of the first current A measured by the main detecting unit 410.

That is, derivation of the first current A by correcting the first current A measured by the main detecting unit 410 and the third current $D_A$ measured by the leakage measuring unit 440 is more accurate than derivation of the accurate first current A by correcting the first current A measured by the main detecting unit 410 and the second current Ad measured by the sub-detecting unit 420.

Thus, the color measuring device 100 of the present invention includes another leakage measuring unit 440 to measure the third current $D_A$ being leaked during the exposure time, and by correcting the first current A and the second current Ad, it is possible to derive a more accurate measured value of the first current A.

Next, referring to FIG. 9, the process of measuring the leakage current from the leakage measuring unit 440 according to the present invention will be described as follows.

Figure 9:
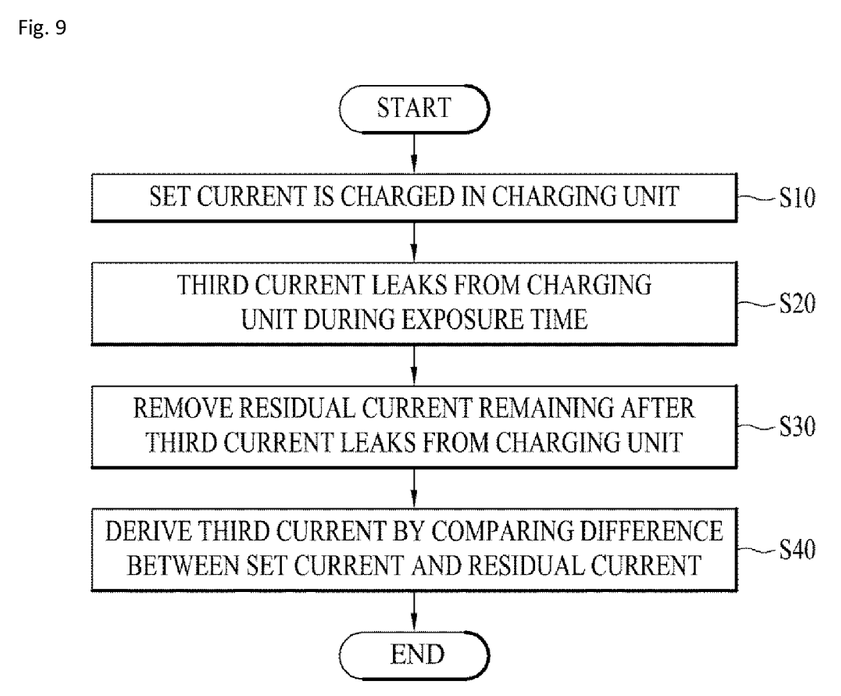
FIG. 9 is a flowchart illustrating a process of measuring the leakage current in the leakage measuring unit of FIG. 6.

FIG. 9 is a flowchart illustrating a process of measuring the leakage current by the leakage measuring unit 440 of FIG. 6.

First, the process passes through the charging process S10 in which a predetermined set current Dc is charged to the charging unit 442 provided in each of the main detecting unit 410 and the sub-detecting unit 420 illustrated in FIG. 6.

Moreover, the leakage setting unit 440 in which the charging unit 442 is charged with the set current Dc by the charging process S10 passes through a first process S20 in which the third current $D_A$ leaks from the set current Dc charged to the charging unit 442 when receiving the light from the incident lens and measuring the first current A by the first measuring unit 414.

At this time, the charging unit 442 according to the present invention is maintained in a state in which the predetermined set current Dc is charged while not measuring the light in the main detecting unit 410.

When the light is incident on the optical detecting unit 412 to measure the first current A in the first measuring unit 414, a part of current leaks from the set current Dc charged to the charging unit 442.

After the completion of the first process S20, the process passes through a second process S30 of removing all the residual current Dd that remains in the charging unit 442. Here, the residual current Dd indicates the amount remaining in the charging unit 442 after leaking of the third current $D_A$ from the set current Dc charged to the charging unit 442.

That is, the first process S20 is a process that occurs during the exposure time when the light is incident on the main detecting unit 410, and the second process S30 and the charging process S10 are processes that occur after the main detecting unit 410 finishes the measurement of the first current A.

Then, the process passes through a derivation process S40 for deriving the third current $D_A$, by comparing the measured residual current Dd removed from the second process S30 with the set current Dc charged to the initial charging unit 442.

Specifically, it is possible to derive the third current $D_A$ as an example of the deriving process S40 by formula 1 below.

$$D_A = D_c - D_d \qquad \text{Formula 1}$$

($D_A$=third current, $D_c$=set current, $D_d$=residual current)

It is possible to measure the third current $D_A$ leaking during the exposure time when measuring the light incident on the main detecting unit 410 through such a process.

Next, a state of deriving the first current A' corrected using the first current A to the third current $D_A$ measured by the color difference meter module 400 according to the present invention will be described referring to FIGS. 10 to 12.

Figure 10:
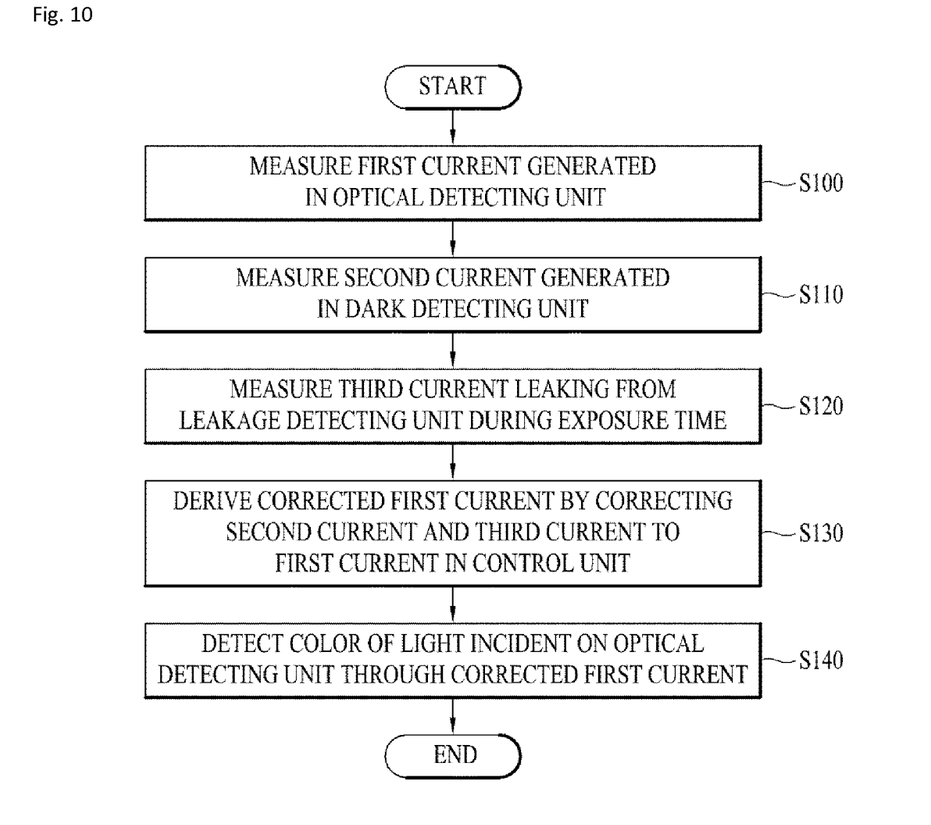
FIG. 10 is a flowchart illustrating a process in which light is incident on the main detecting unit of FIG. 6 to correct the detected stimulus value.
Figure 11:
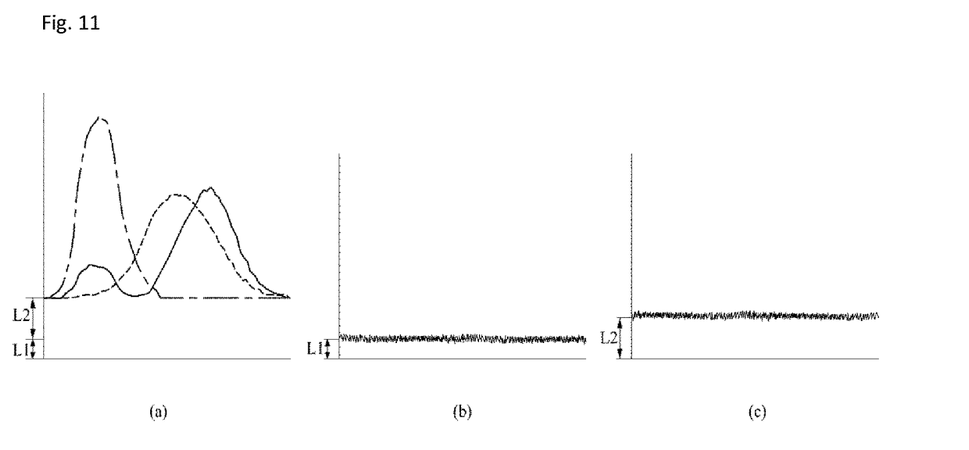
FIG. 11 is a graph illustrating the stimulus values generated by the current detected by each of the main detecting unit, the sub-detecting unit, and the leakage measuring unit in the color difference meter module of FIG. 2.
Figure 12:
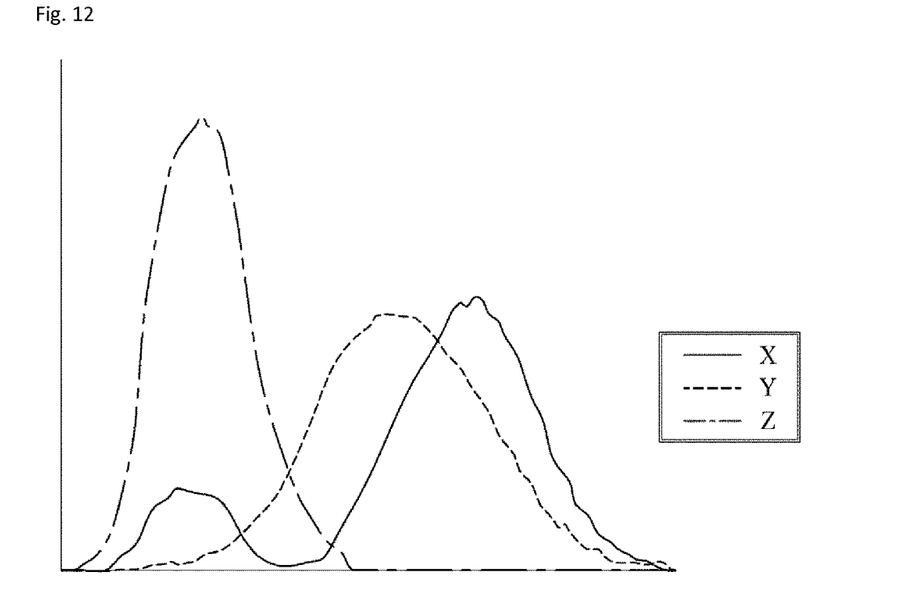
FIG. 12 is a graph illustrating the stimulus value indicated by correcting the detected signal of FIG. 11 in the control unit.

FIG. 10 is a flowchart illustrating a process of correcting the stimulus value detected by light incident on the main detecting unit 410 of FIG. 6, FIG. 11 is a graph illustrating stimulation values generated by the current detected in each of the main detecting unit 410, the sub-detecting unit 420, and the leakage measuring unit 440 in the color difference meter module 400 of FIG. 2, and FIG. 12 is a graph of the tristimulus values illustrated by correcting the detected signal of FIG. 11 in the control unit.

First, when measuring the color of the light in the color difference meter module 400, the first current A generated by light incident on the light detecting unit 412 is measured by the first measuring unit 414 (S100).

At the same time, the second current Ad generated in the dark detecting unit 422 by the external environment factors is measured by the second measuring unit 424 (S110).

In addition, the third current $D_A$ leaking from the charging unit 442 during the exposure time is measured by the leakage measuring unit 440 (S120).

Thus, each of the first current A to the third current $D_A$ is independently measured, and the measured information of the first current A to the third current $D_A$ is transmitted to the control unit.

Thereafter, the control unit corrects the second current Ad and the third current $D_A$ to the first current A to derive the corrected first current A (S130). Here, the corrected first current A' is corrected by applying the value of the third current $D_A$ leaking by the configuration such as the value of the second current Ad generated by the external environmental factors and the amplification circuit 414a to the first current A measured by the first measuring unit 414.

Thus, the color of the light incident on the optical detecting unit 412 is detected through the first current A' that is corrected by the control unit (S140).

More specifically, FIG. 11a illustrates the tristimulus values using the first current A measured by the main detecting unit 410, and FIG. 11b illustrates the value of the second current Ad measured by the sub-detecting unit 420.

FIG. 11c illustrates the value of the third current $D_A$ measured by the leakage measuring unit 440.

It is possible to know from FIG. 11b that the second current Ad having the numerical values higher by L1 than the reference value of the initially input zero point is detected. Although the second current Ad obtained by measuring the values to be input in the dark state in theory should be identical to the initially input reference value, unlike this, the second current Ad including the varied numerical values detected in the sub-detecting unit 420 is detected by the external environmental factors.

Then, referring to FIG. 11b, it illustrate the amount of the third current $D_A$ leaking from the main detecting unit 410 or the sub-detecting unit 420, and is possible to know that the third current $D_A$ having the numerical value higher by L2 than the zero point is detected. If the leakage current is not generated, although the third current $D_A$ becomes zero and should not be detected, the leakage current is generated by the structural features such as the amplification circuit 414a and the third current $D_A$ is detected, and this changes to be sensitive to the external environmental factors.

Here, since the main detecting unit 410, the sub-detecting unit 420, and the leakage measuring unit 440 are configured to receive the influences of the same external environmental factors, this means that the numerical values varied by the external environmental factors are included in the value of the first current A measured by the first measuring unit 414.

Thus, the control unit derives the corrected first current A', by reflecting the L1 value of the second current Ad measured by the second measuring unit 424 and the value L2 of the third current $D_A$ measured by the leakage measuring unit 440 to the first current A measured by the first measuring unit 414.

As an example of deriving the corrected first current A' by the control unit, the following formula 2 can be applied.

$$A'=A-A_d-D_A \qquad \text{Formula 2}$$

(A'=corrected first current as, A=first current, Ad=second current, $D_A$=third current)

By deriving the corrected first current A' through such a process, it is possible to accurately detect the color of the light incident on the main detecting unit 410.

Thus, by deriving the corrected first current A' that is corrected by the control unit using the first current A to the third current $D_A$, as illustrated in FIG. 12, it is possible to accurately measure the color of the light that is purely incident from the incident lens module 200.

Since the color difference meter module 400 according to the present invention is provided, it is possible to measure the accurate color through relative comparison between the detected first current A, the second current Ad, and the third current $D_A$, without passing through a separate zero point adjustment process.

In particular, conventionally, since the color is measured after performing a separate zero point adjustment, the time difference between the zero point adjustment time and the color measurement point occurs, and thus the accuracy of the color to be measured decreases. However, according to the present invention, the main detecting unit 410 and the sub-detecting unit 420 measure the first current A and the second current Ad at the same time without individually performing the zero point adjustment, and the leakage measuring unit 440 measure the third current $D_A$. Thus, the value detected by the time difference does not change, and the accuracy and reliability of the measured color increase.

As described above, although preferred embodiments of the present invention have been described, in addition to the embodiments described above, it can be embodied in other forms without departing from the spirit or category of the present invention. Therefore, the embodiments should be considered as being illustrative rather than restrictive to the specific forms and, accordingly, the present invention is not limited to the above-mentioned description, and may be varied within the scope of the category of the appended claims and their equivalents.

DESCRIPTION OF REFERENCE NUMERALS

100: color measuring device
200: incident lens module
300: case
400: color difference meter module
410: main detecting unit
420: sub-detecting unit
430: filtering unit
440: leakage measuring unit
500: optical distribution module

What is claimed is:

1. A color measuring device comprising:
a case having a light sensing space formed therein;
an incident lens module that is configured by continuous arrangement of a plurality of lenses in an inward direction on one side of the case and is disposed in a region in which light is emitted from a measuring target to transmit the emitted light into the interior; and
a color difference meter module that includes a main detecting unit having an optical detecting unit configured to receive the light introduced from the incident lens to generate current depending on the color and a first measuring unit configured to measure a first current generated by the optical detecting unit, a sub-detecting unit having a dark detecting unit disposed adjacent to the main detecting unit and blocking light to generate a current in the dark state and a second measuring unit configured to measure a second current generated by the dark detecting unit, a leakage measuring unit that has a charging unit provided in the second measuring unit and charged with a predetermined set current and measures a third current leaking from the charging unit, and a control unit that corrects the first current by reflecting the second current measured by the sub-detecting unit and the third current measured by the leakage measuring unit,
wherein the charged current in the charging unit decreases during the time at which the main detecting unit and the sub-detecting unit receive light to generate the first current, and the third current leaks.

2. The color measuring device of claim 1, wherein in the leakage measuring unit,
while receiving the light from the incident lens to measure the color, the third current leaks from the set current charged to the charging unit,
after completion of the color measurement, all the residual current remaining in the charging unit is removed, and the set current is charged to the charging unit again.

3. The color measuring device of claim 2, wherein the leakage measuring unit measures a difference between the set current and the residual current to detect an amount of the leaked third current.

4. The color measuring device of claim 1, wherein the first measuring unit includes a leakage measuring unit having the same shape as the second measuring unit.

5. The color measuring device of claim 1, wherein the sub-detecting unit is affected by the same conditions as the main detecting unit affected by external factors.

6. The color measuring device of claim 1, wherein the main detecting unit includes at least three or more optical detecting units, and each of them is configured to detect light of wavelengths different from each other.

7. The color measuring device of claim 6, wherein the color difference meter module further includes
a connector that is disposed in front of the main detecting unit and includes a communication port that is in communication with the main detecting unit to transmit the incident light to the main detecting unit;
a color filter that is provided inside the communication port to transmit only light of a specific wavelength of the incident light; and
a filtering unit that causes the light incident on each of the optical detecting units to have wavelengths different from each other.

8. The color measuring device of claim 6, further comprising:
an optical distribution module provided between the incident lens module and the color difference meter module to distribute and transmit the light incident from the incident lens module to the color difference meter module.

9. A color difference meter module comprising:
a main detecting unit that includes an optical detecting unit configured to receive the light introduced from an incident lens to generate current depending on the color, and a first measuring unit configured to measure a first current generated by the optical detecting unit;
a sub-detecting unit that is disposed adjacent to the main detecting unit and includes a dark detecting unit configure to block light to generate a current in a dark state, and a second measuring unit configured to measure a second current generated by the dark detecting unit;
a leakage measuring unit that includes a charging unit provided in the second measuring unit and charged with a predetermined set current, and measures a third current leaking from the charging unit; and
a control unit that corrects the first current by reflecting the second current measured by the sub-detecting unit and the third current measured by the leakage measuring unit,
wherein the charged current of the charging unit decreases depending on a change in time at which the main detecting unit and the sub-detecting unit receive light to generate the first current, and the third current leaks.

10. The color difference meter module of claim 9, wherein the leakage measuring unit measures the leaked third current,
by passing through a first measurement process in which the third current leaks from the set current charged to the charging unit while receiving the light from the incident lens to measure the first current by the first measuring unit, and
a second measurement process in which all the residual current remaining in the charging unit is removed after completion of the first measurement process.

11. The color difference meter module of claim 10, wherein the leakage measuring unit measures a difference between the set current and the residual current to measure the leaked third current.

12. The color difference meter module of claim 10, wherein the third current is derived by following Formula 1, $$D_A = D_c - D_d$$  Formula 1

($D_A$=third current, $D_c$=set current, and $D_d$=residual current).

13. The color difference meter module of claim 9, wherein the control unit corrects the first current using the second current and the third current, and measures the color of the light incident on the main detecting unit from the incident lens through the corrected first current.

14. The color difference meter module of claim 9, wherein the control unit measures the color of the light incident on the main detecting unit by correcting the first current by Formula 2 below, $$A' = A - A_d - D_A$$  Formula 2

($A'$=corrected first current, $A$=first current, $A_d$=second current, and $D_A$=third current).

15. The color difference meter module of claim 9, wherein the first measuring unit is provided with the leakage measuring unit of the same shape as that provided in the second measuring unit.

16. The color difference meter module of claim 9, wherein the sub-detecting unit is affected by the same conditions as the main detecting unit affected by external factors.

17. The color difference meter module of claim 9, wherein the main detecting unit includes at least three or more first detecting units, and each of them is configured to detect light of wavelengths different from each other.

18. The color difference meter module of claim 9, wherein the color measuring device further includes a separate filtering unit that is installed in front of the main detecting unit to cause the light incident on each of the optical detecting units to have wavelengths different from each other.

19. The color difference meter module of claim 18, wherein the filtering unit comprises:
a connector that is installed in front of the main detecting unit, and includes a communication port that is in communication with the main detecting unit to transmit the incident light to the main detecting unit; and
a color filter that is provided inside the communication port to transmit only light of a specific wavelength of the incident light.

* * * * *